(12) United States Patent
Reed

(10) Patent No.: US 12,303,250 B2
(45) Date of Patent: May 20, 2025

(54) BIDIRECTIONAL INCENTIVE SPIROMETER

(71) Applicant: George Reed, Lake Oswego, OR (US)

(72) Inventor: George Reed, Lake Oswego, OR (US)

( * ) Notice: Subject to any disclaimer, the term of this patent is extended or adjusted under 35 U.S.C. 154(b) by 759 days.

(21) Appl. No.: 17/335,434

(22) Filed: Jun. 1, 2021

(65) Prior Publication Data

US 2021/0282664 A1     Sep. 16, 2021

Related U.S. Application Data

(63) Continuation-in-part of application No. 16/162,343, filed on Oct. 16, 2018, now Pat. No. 11,045,112, which is a continuation-in-part of application No. 14/938,805, filed on Nov. 11, 2015, now abandoned.

(51) Int. Cl.
| | | |
|---|---|---|
| *A61B 5/087* | (2006.01) | |
| *A61M 11/00* | (2006.01) | |
| *A61M 15/00* | (2006.01) | |
| *A61M 16/00* | (2006.01) | |
| A61B 5/091 | (2006.01) | |

(52) U.S. Cl.
CPC ............. *A61B 5/087* (2013.01); *A61M 11/00* (2013.01); *A61M 15/00* (2013.01); *A61M 16/00* (2013.01); *A61M 2205/3334* (2013.01); *A61M 2205/3584* (2013.01); *A61M 2205/52* (2013.01); *A61M 2205/587* (2013.01); *A61M 2205/8206* (2013.01); *A61M 2230/40* (2013.01)

(58) Field of Classification Search
CPC ...... A61B 5/087; A61B 5/0935; A61M 11/02; A61M 11/06; A61M 2205/3334; A61M 2205/52; A61M 2230/40
See application file for complete search history.

(56) References Cited

U.S. PATENT DOCUMENTS

2020/0330719 A1* 10/2020 Segal ................... A61B 5/4833
2021/0146079 A1*  5/2021 Alizoti ................ A61M 15/009

OTHER PUBLICATIONS

Mercury Medical Product Catalog; https://www.mercurymed.com/catalogs/RDR_Connectors_Adapters.pdf; accessed Feb. 23, 2024; published Dec. 5, 2014. (Year: 2014).*

* cited by examiner

*Primary Examiner* — Daniel J Colilla
(74) *Attorney, Agent, or Firm* — Mark S Hubert

(57) ABSTRACT

A respiratory therapy device that is adapted to matingly, frictionally connect with dimensionally standardized devices and device adaptors, that when combined, allow for respiratory treatments. It monitors the direction of the air and or medicament flow (gases) in the device and can visually report as well as record the number of PEP treatment events or the number of medicament administrations by utilizing at least one bidirectional motion sensor therein. It presents a resettable, visual indicator for each pulse of gas that passes along its interior passage as well as providing a stored and transmittable record of these pulmonary events. It has an energy saving mode that will only allow the unit to be powered for operation when it is being handled.

19 Claims, 7 Drawing Sheets

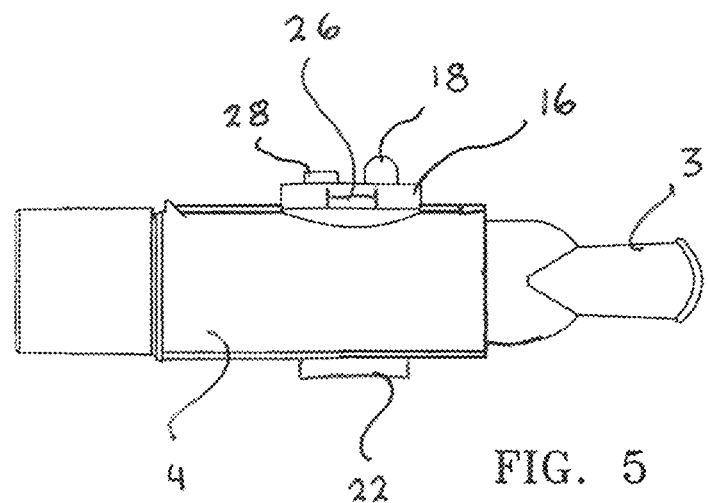
FIG. 5
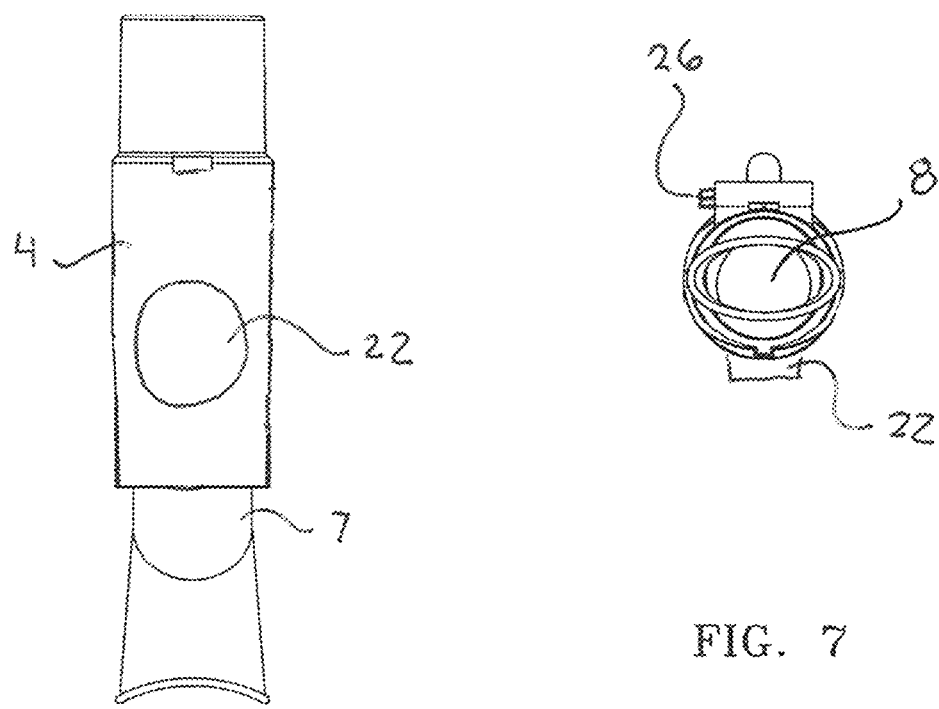
FIG. 6
FIG. 7

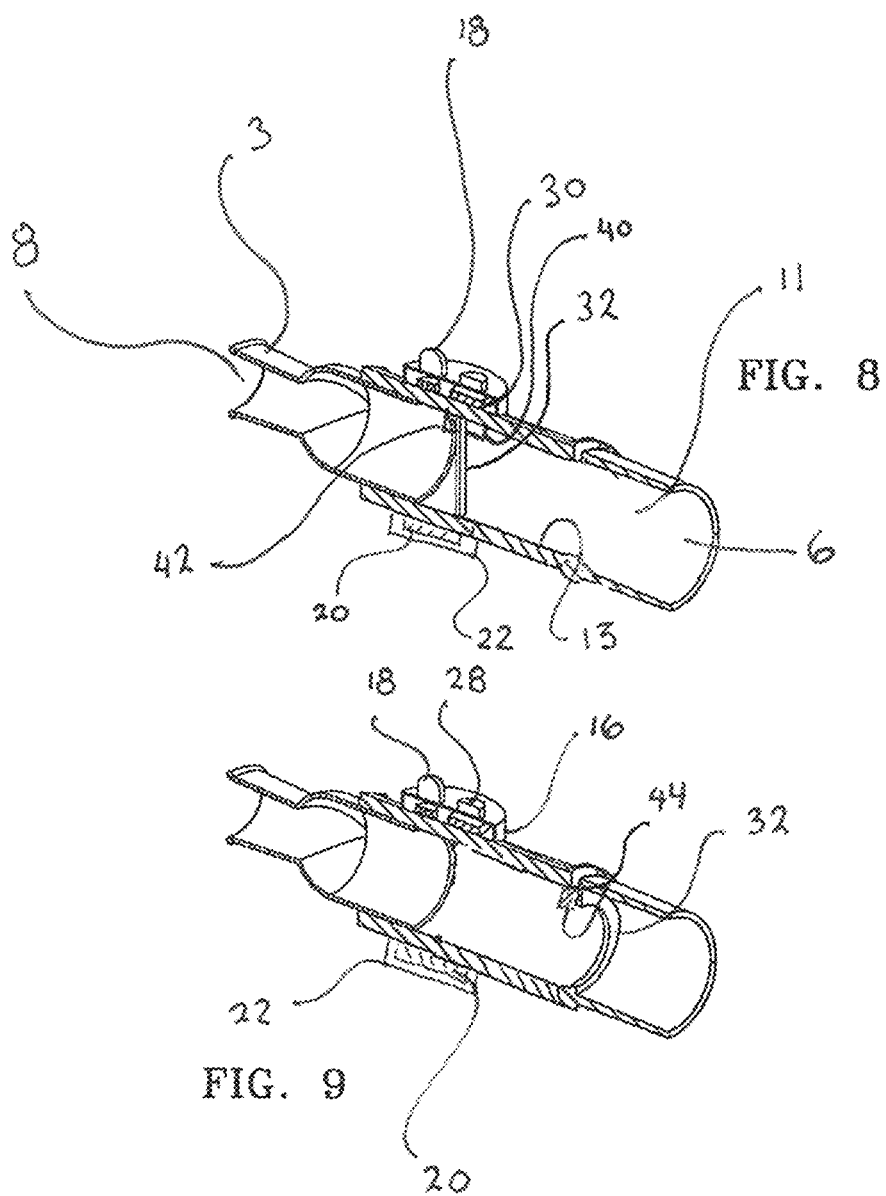

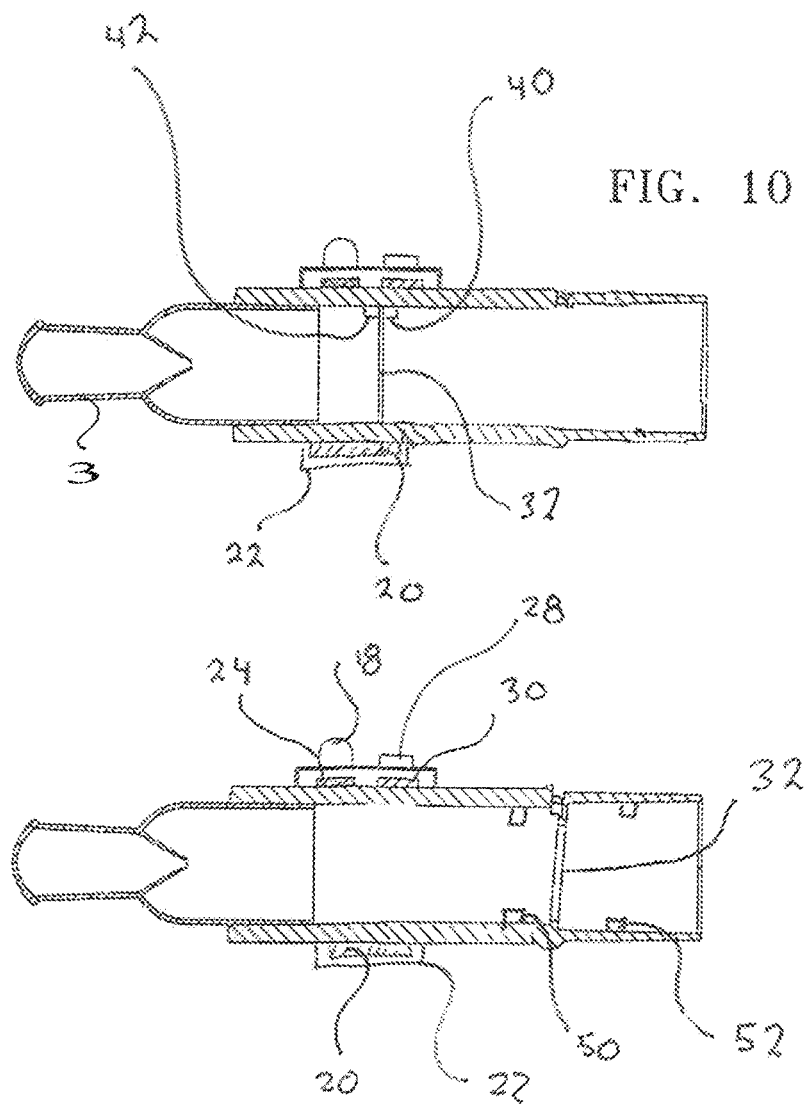

BIDIRECTIONAL INCENTIVE SPIROMETER

CROSS REFERENCE TO RELATED APPLICATIONS

This application incorporates in its entirety, and claims the benefit of priority from pending U.S. Utility patent application Ser. No. 16/162,343 filed Oct. 16, 2018 and entitled "INCENTIVE SPIROMETER" which claims domestic priority from abandoned U.S. Utility patent application Ser. No. 14/938,805 filed Nov. 11, 2015 and entitled "RESPIRATORY MEDICAMENT AND THERAPY DATA SYSTEM AND METHOD OF USE."

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to medical respiratory devices, and more particularly to respiratory patient incentive spirometer technology.

BACKGROUND

Respiratory treatments vary considerably as do the different manufacturer's devices used to facilitate the treatments. Generally, the patient undergoes separate regimens of positive exhalation pressure (PEP) treatments and medicament inhalation (drug delivery). First, the exhalation treatment requires the patient to exhale through any of a plethora of devices that send a resultant pulsation pressure wave back down into their lungs to dislodge phlegm. Second, once enough cycles have been performed, the patient's breathing ability is improved and they can undergo an inhalation treatment wherein they receive a medicated aerosol (generally inhaled antibiotics, bronchodilators, corticosteroids) to further increase their lung capacity and ease their labored breathing. This type of drug delivery is most effective immediately after the exhalation treatments are performed. Switching between devices to accomplish these two tasks, often requires connection to multiple transition components and mouthpieces, which increases the connection complexity and robs precious time between treatments.

Keeping track of the actual numbers, duration and length of the respiratory treatments is an important factor in determining further treatment regimens. Generally, it requires some level of medical staff, be it a doctor, nurse or technician, to both ensure the treatments are performed to satisfaction and on the correct schedule. Knowing this, along with the patient's progress, allows the medical staff to alter the treatment plan accordingly. This information is indispensable but often not available where the trained patient self-administers.

Prior art devices that have tried to combine the two types of respiratory therapies have failed in maintaining a high percentage of the flow of the medicinal aerosol particles in the desirable 0.5 to 4.5-micron diameter. Some of the larger aerosol particles are lost in the exhalation phase where they are swirled around in the device to collide and condense. In devices that utilize a valve system, aerosol particles collide with any valve therein as it opens in the inhalation therapy phase. All these mechanisms reduce the amount of medicated aerosol particles that are delivered to the patient and increase the average size of the aerosol particles delivered. A straight line Laminar gas flow is the optimal route for intake or expulsion of gases to minimize friction, particle impingement and condensation of the medicament in the related equipment.

There are other inherent problems with positive exhalation pressured devices. These are quite exhausting for many patients and because of their diminished lung capacity, successful exhalations (events) often leaves them out of breath and gasping for air. Often the patient does not exhale with enough pressure to achieve the desired effect of loosening the phlegm and opening the pulmonary pathways for inhaled drug delivery. In this case the delivered drug does will be inadequate and the patient's progress will be slower. Unfortunately, with conventional devices the medical staff as well as the patient have no way of knowing what part of the treatment, the PEP or drug delivery, is responsible for the slow progress.

One of the problems with either the administration of an inhalation drug or the performance of a lung-clearing device is because of their high frequency, they are usually performed by the patient. Patients often do not follow the prescribed routines and often do not perform the correct number or events or perform the events correctly. This is especially true where they receive no feedback as to how their treatments are being performed. If medical personnel are not present no corrective action is taken.

A novel design for a respiratory interface or intermediary apparatus, capable of connection with a diversity of respiratory devices that provides efficiency in treatment compliance, product delivery and data recording would fulfill a long felt need in the respiratory treatment industry. This new invention utilizes and combines known and new technologies in a unique and novel configuration to overcome the aforementioned problems and accomplish this.

BRIEF SUMMARY

In accordance with various embodiments, an incentive spirometer that encourages patients to practice the actions prescribed to keep their lungs healthy, is provided.

In one aspect, a device that provides a visual stimulus (a reward) and optional data record of the direction, duration, pressure and number of gas pulse flow events (medicament inhalation or PEP exhalation) that occur within the device during a lung-clearing and treatment pulmonary regime, is provided.

In another aspect, a device that algorithmically analyzes the gas pulse flow data so as to provide a data record of patient treatment that can be appended to their medical history for evaluation against their treatment progress by medical personnel is provided.

In yet a final aspect, a liner, bidirectional incentive spirometer that enables a new level of efficiency in charting patient progress, medicament delivery, patient follow-up, therapy session data and the like that is adapted to matingly connect with all standardized respiratory devices commonly utilized in all lung and respiratory disease treatment, testing, rehabilitation, medicament delivery and life support devices.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

FIG. 5 is a left side view of the bidirectional incentive spirometer;

FIG. 6 is a bottom view of the bidirectional incentive spirometer;

FIG. 7 is an end view of the proximal end of the bidirectional incentive spirometer;

FIG. 8 is a perspective left side cross sectional view of the first embodiment bidirectional incentive spirometer;

FIG. 9 is a perspective right side cross sectional view of the second embodiment bidirectional incentive spirometer;

FIG. 10 is a right side cross sectional view of the third embodiment bidirectional incentive spirometer;

FIG. 11 is a right side cross sectional view of the fourth embodiment bidirectional incentive spirometer;

DETAILED DESCRIPTION

Figure 1:
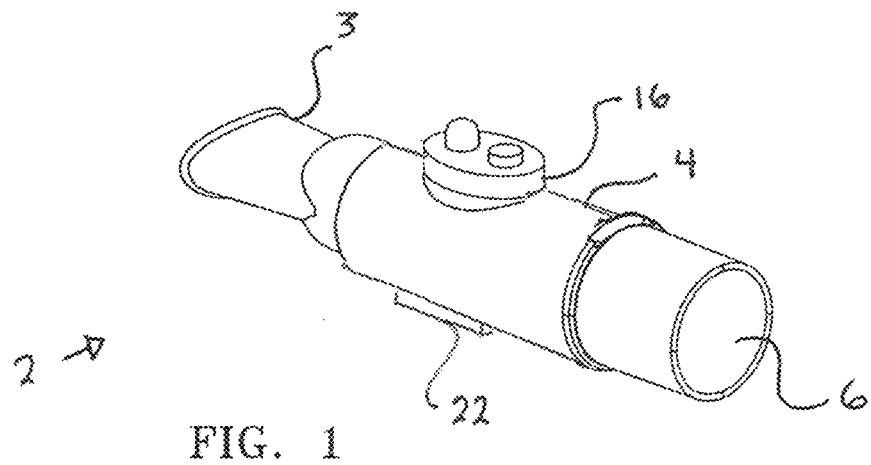
FIG. 1 is a right side perspective view of the bidirectional incentive spirometer.
Figure 2:
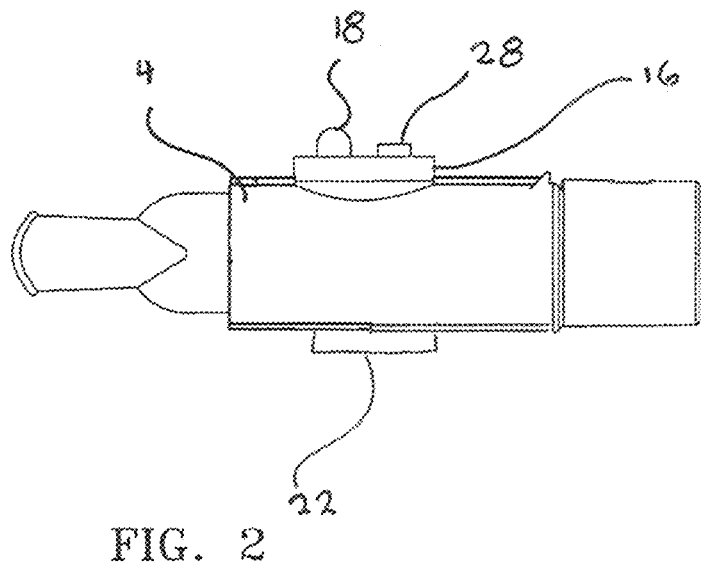
FIG. 2 is a right side view of the bidirectional incentive spirometer.
Figure 3:
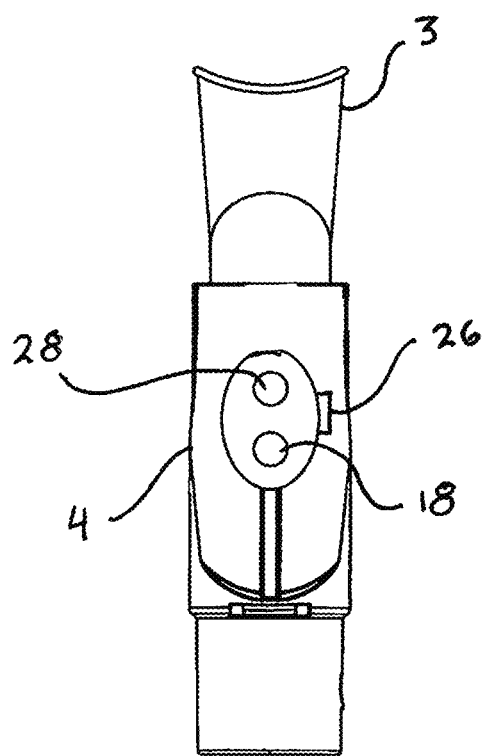
FIG. 3 is a top view of the bidirectional incentive spirometer.
Figure 4:
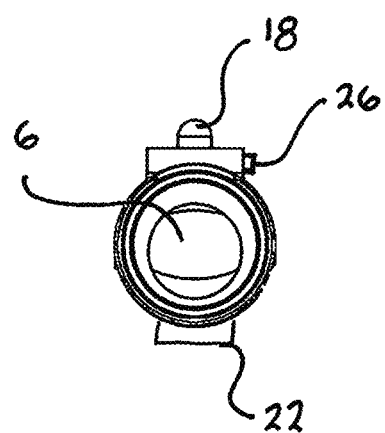
FIG. 4 is a distal end view of the bidirectional nebulizer end of the incentive spirometer.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention. It will be apparent to one skilled in the art, however, that other embodiments of the present invention may be practiced without some of the disclosed details. It should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

The terminology used in the description of the bidirectional incentive spirometer herein is for the purpose of describing particular embodiments only and is not intended to be limiting of the inventive concept. As used in the description of the bidirectional incentive spirometer and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "PEP" or "PEP device" refers to a positive expiratory pressure device that provides resistance to the exhalation of breath. This forces respiratory patients to exhale hard into it, increasing the time to empty the lung's capacity against the resistance. This acts as an airway clearance technique to help air get behind the mucus to move it from lung and airway walls. It also holds airways open, keeping them from closing. There are oscillating and non-oscillating PEP devices of varying designs.

As used herein, the term "delivered drug dose" refers to the aggregate amount of aerosol medicament determined to have reached the patient's lungs in a single drug delivery treatment/session. This is can be roughly calculated knowing how many breaths the patient took, the duration of the breaths, the concentration of the aerosol and the efficiency of the drug delivery device considering the aerosol attenuation.

As used herein, the term "inhalation drug delivery device" refers to any one of a group devices that disperse an aerosol or powder pulmonary medicine. These come in various designs such as nebulizers, pressurized metered-dose inhaler (pMDI), and dry powder inhalers (DPIs).

As used herein, the terms "microprocessor" means a computer processor on a microchip that contains all, or most of, the central processing unit (CPU) functions and is the "engine" that goes into motion when the motion sensor sees movement. It may incorporate a real time clock and either or both of volatile/nonvolatile memory and performs algorithmic and logic operations based on input signals or data from integrated devices such as the motion sensor, or manually operated electrical switches. It outputs operational signals that integrates with other electrical circuits. It may also output algorithmically derived data to an external computing device. (This may be a local computer, tablet, smart phone, or a health provider's network via a remote server.) These operations are the result of a set of instructions that are part of the microprocessor design as is well known in the industry. In simple terms, the microprocessor is a multipurpose, programmable device that accepts digital data as input, processes it according to instructions stored in its memory, and provides results as output. It may have an integrated wireless transceiver for transmission to an accepting application installed on the smart phone, tablet or computing device, or it may utilize an data port such as a USB port for the direct connection of data transfer to a data storage device such as a thumb drive, memory stick, computer hard drive or data chip.

As used herein, the term "motion sensor" refers to any electro-mechanical or electronic device that provides an electric signal to, or modulates electricity to a microprocessor upon movement or elastic deformation of its sensing element. It may comprise a sensing element or the combination of a sensing element and a transducer or other device such as IR switches to generate an electric signal based on the movement of the sensing element. The motion sensor's sensing element is placed in or along the interior cavity of the body of the device 2 and moves or elastically deforms under the flow of the gas pulses passing in either direction along the central cavity of the bidirectional incentive spirometer. Common motion sensors for gases include Hall effect sensor devices, heated anemometers, bidirectional resistive strain sensors, flexible diaphragm pressure switches, swing make or break contact switches, pivotable fibers or strands, bidirectional accelerometers, IR radio frequency beam sensors and the functional equivalents, alone or in any combination thereof. The sensing element may be directly connected to the microprocessor or may have an active or passive transducer connected to the sensing element that translates the motion of the sensing element into an electric signal that provides the direction, duration and optionally the magnitude of the gas pulse flow down the internal cavity of the bidirectional incentive spirometer to the microprocessor.

As used herein, the term "transducer" refers to any mechanical, electrical, electronic or electro-mechanical device that either passively or actively translates the motion or position of a sensing element into an electric signal that it provides to the microprocessor which the microprocessor can convert into stored data reflective of the direction, duration, and time of the occurrence of the gas pulse flow event.

As used herein, the term "personal mobile device" refers to a device that is both portable and capable of collecting, storing, transmitting or processing electronic data or images. Examples include laptops or tablet PCs, personal digital assistants (PDAs), and "mobile smart" phones. This definition also includes storage media, such as USB hard drives or memory sticks, SD or CompactFlash cards, and any peripherals connected to the device.

As used herein, the term "smartphone" means any web-enabled mobile phone. While the term "smartphone" is well known in the art, smartphones typically include a touch sensitive screen, a messaging client, global positioning systems (GPS) technology or any other geo-position mechanisms to determine the physical coordinates of the smartphone, and a browser application. The browser application employs any web-based language such as JavaScript Object Notation (JSON), JavaScript, HyperText Markup Language (HTML), or any other web-based programming language capable of sending and displaying messages, search queries, and search query results.

As used herein, the term "cycle initiation switch" refers to an ON/OFF switch that powers the device from its battery. It may be a simple mechanical switch on the outside of the device that is activated by tactile manipulation, or it may be an internal magnetic switch activated by the removal of a magnet from the outside of the device. In other embodiments, the cycle initiation switch may be an accelerometer thereon or therein the device, that upon the sensing of motion of the device switches power to the microprocessor. The accelerometer may be used in conjunction and downstream of another cycle initiation switch to help maintain the battery life. In this type of design, although the cycle initiation switch has been turned or left on, the microprocessor and associated electronics will not to be powered until the device has been picked up and ready for use.

The present invention relates to a novel design for a linear, bidirectional incentive spirometer 2 that will present a pulmonary patient with visual feedback at every event that they successfully complete and optionally, provide a data record of the gas flows therethrough for review by medical personnel. These data records are transmittable to a personal mobile device with the associated application installed thereon directly or wirelessly. It allows the connection of an airway clearance device (here, as an example, a "PEP" device), an inhalation drug delivery device (that uses an inhalation to deliver a medical powder or aerosol) or other pulmonary equipment such as a ventilator or respirator or gas supply. The device has a proximal (patient mouthpiece) end and a distal (connected device) end with the same or different IDs and ODs but of standardized ISO dimensions. In the preferred embodiment the proximal end of the device has an 15 mm ID (female) port and the distal end has a 22 mm OD (male) port.

Since pulmonary equipment have standardized end coupling sizes, generally with ISO 22 mm ID, ISO 22 mm OD, 15 mm ID or 15 mm OD dimensions, there are copious adapter sleeves available in the industry to connect equipment with different sized end couplings. This has the benefit of allowing the quick connection, either directly or indirectly, of the device 2 with an adaptor sleeve, to any of the above devices. Consequently, the device 2 may have the same sized ends or different sized ends, and with the use of reducing or increasing adapter sleeves, can be connected at either the proximal or distal end to any piece of pulmonary equipment.

Currently patients with lung disorders and respiratory ailments undergo testing, medicament delivery, monitoring, phlegm dislodgment therapy, lung expansion therapy and other related medical procedures. Many of these are done in the hospital under medical supervision, while others may be as simple as a nebulizer aerosol medicament session or a PEP regime performed at home. The efficiency of the implementation of these treatments can only be determined analyzing data not generally collected and that possibly may only be orally reported. The overall actual physical results of these treatments are sometimes charted, however there is no ongoing complete record of the performance of each of these treatments for future trending analyses. This is a huge downfall of respiratory disorder treatments. Because they occur so frequently and often unsupervised, the overall effect or progress of these treatments is not always discernable, even to those medically trained in the industry. One reason, is that the patient may not follow the treatment schedule, may not complete each gas flow event, or may not be able to generate enough pressure or suction with their breath. Alzheimer's patients frequently need retraining in how and when to conduct their personal home treatments. The inability of the respiratory disease treatment industry to tabulate the actual medicament delivered to a patient's lungs, or how often they actually and correctly used their PEP device is a huge downfall that this linear, bidirectional, positive inhalation spirometer can remedy.

This linear, bidirectional incentive spirometer 2, provides a respiratory medicament and therapy data system that can reward the patient with a visual stimulus upon correct usage and also provides respiratory data to reflect the therapy sessions and treatments conducted.

Looking at FIGS. 1 to 7, it can be seen that the incentive spirometer 2 (device) has a linear, cylindrical, hollow polymer body 4 with a distal (connected device) end port 6 and a proximal (patient) end port 8. These two ports 6 and 8, reside centered about the linear axis, of the device 2 to allow a straight, laminar flow, minimal resistance pathway for the flow of gas pulses in either direction. The internal cavity 11 of the device 2 has a smooth internal face 13 to minimize condensation of moisture in exhaled breath, to minimize the condensation of the atomized medicament and to facilitate the sterilization of the device 2. (See FIG. 8) The minimum Ra or arithmetic average roughness value for the internal face 13 is 8 Ra or 3 microns. The preferred embodiment has a surface roughness range of 3-9 Ra.

The proximal end port 8 is designed to accept a standardized replaceable mouthpiece 3 and in the preferred embodiment is configured as a female ISO 15 mm circular inner diameter port 8. Into this 15 mm port is frictionally inserted a mouthpiece 3 having a matingly engageable male 15 mm OD distal end 7 and an oval proximal end 9 that the patient places in their mouth. Other size matingly engageable configurations work equally as well, however, an 15 mm OD patient mouthpiece is the most prevalent size in the industry. The actual OD and ID may be varied during fabrication or may be adjusted through the use of a reducing or increasing adapter.

The distal end port 6 is designed for connection to a plethora of different pulmonary treatment devices, primarily a PEP device or an inhalation drug delivery device. The preferred embodiment is configured as a tapered male ISO 22 mm circular OD for connection with industry standard nebulizers and similar functioning devices. The outer surface of the distal end port 6 of the body 4 is circular and unadorned. The outer tapered configuration of the distal end port 6 allows for an extra secure connection with any PEP device, which is important because there is a backpressure developed during patient exercises trying to dislodge the PEP device from the bidirectional incentive spirometer 2. Again, other dimensions of matingly engageable configurations will work equally as well, however, a 22 mm OD is the most prevalent size in the industry.

Figure 13:
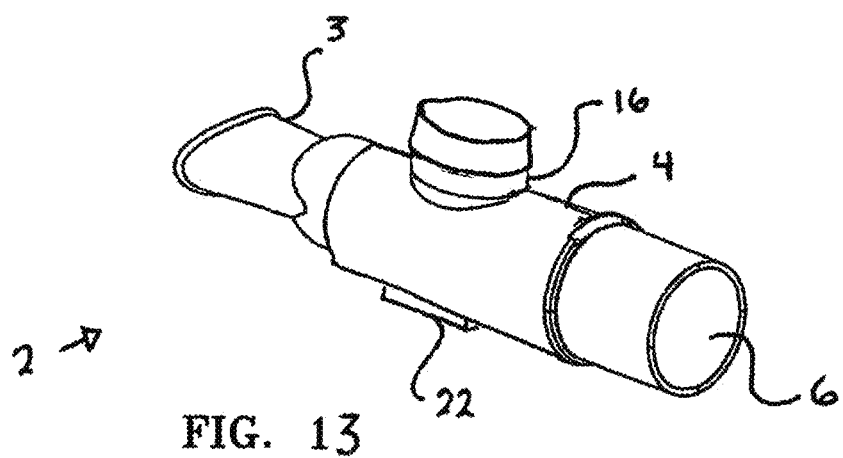
FIG. 13 is a right side cross sectional view of the first embodiment bidirectional incentive spirometer without the LED and using a different switch; modify FIG. 8
Figure 14:
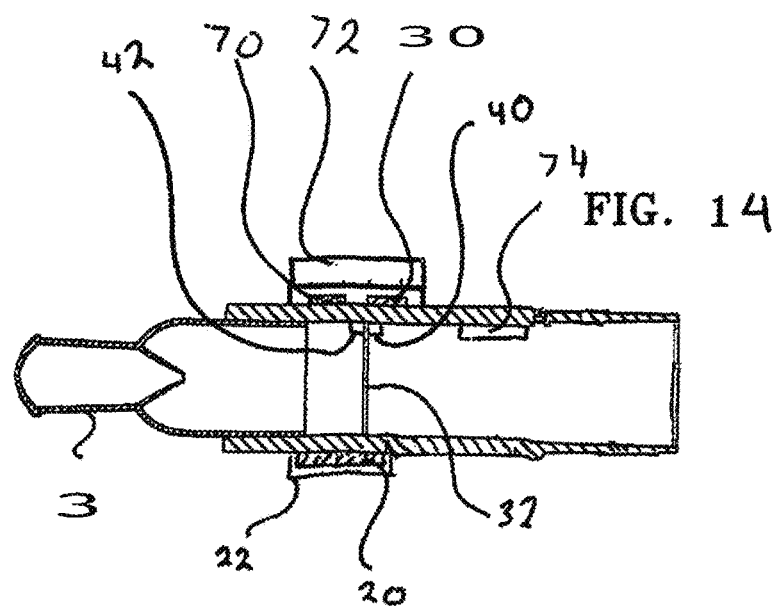
FIG. 14 is a right side view of the first embodiment bidirectional incentive spirometer without the LED and using a different switch modify FIG. 1

Looking at FIGS. 3-12 it can be seen that on the body 4 of the incentive spirometer 2, preferably between the proximal end port 8 and the distal end port 6 is a top exterior housing 16 that contains a microprocessor 30, a wireless transceiver 24, an optional LED 18, a cycle initiation switch 28, and a data transfer port 26 (FIGS. 3 and 5) (preferably USB) the last three which protrude through the top exterior housing 16. In other embodiments the microprocessor 30 may have the wireless transceiver 24 incorporated therein/thereon, the cycle initiation switch may be a magnetic switch and it may use an accelerometer switch to save battery power. (FIGS. 13 and 14)

These housed components are operationally connected to the battery 20 and the motion sensor either by direct connection to the sensing element 32 or by indirect connection through an intermediary transducer 12, depending on the design and type of motion sensor used.

While the preferred location of the top exterior housing 16 is the top of the body 4 above the motion sensor (sensing element 32 with or without a connected transducer 12) for ease of fabrication and tactile operation, the top external housing 16 may optionally be located elsewhere on the device 2. The motion sensor may be corrected to the top housing to make a single unit that may be connected into the top of the device body 4 via an orifice. This simplifies construction and installation/assembly of the device 2.

There is a bottom housing 22 that contains the battery 20 used to power the motion sensor, the LED 18, the microprocessor 30 and the wireless transceiver 24. The preferred embodiment uses a replaceable coin battery 20, although a rechargeable battery 20 may be optionally installed and a charging port incorporated into the bottom housing 22. These wired electrical connections will be made as is well known in the industry using wire raceways therein or thereon the device body 4.

FIG. 8 shows the first embodiment bidirectional incentive spirometer utilizing a lightweight pivotable fiber used as the sensing element 32 suspended vertically in the internal cavity 5 beneath the top housing 16. This sensing element 32 can pivot toward the proximal end 8 or the distal end 6 of the device 2 depending on the direction of the gas pulse flow. It will remain vertical with no flow and remain angled toward the direction of the gas pulse flow as long as the flow exists. As the pivotable fiber swings toward the distal end (during phlegm clearing exercises) or toward the proximal end (during medicament delivery) the distal transducer 40 or the proximal transducer 22 is actuated and sends a signal to the microprocessor 30 indicating direction of gas pulse flow and the duration of the gas pulse flow. The microprocessor 30 then can distinguish an exercise from a medicament delivery, and having its own internal time clock records each in the series of these events by date, time and duration.

FIG. 9 shows the second embodiment bidirectional incentive spirometer wherein the sensing element 32 is a strain gauge with its associated strain gauge transducer 44. Here it is of a circular ring configuration to minimize the restriction for the flow of gas pulses down the internal cavity of the device 2. It is located at a different location along the internal cavity of the device than is the sensing element 32 of the first embodiment, although it may be located anywhere along the path of the gas pulse flow.

FIG. 10 shows the third embodiment bidirectional incentive spirometer utilizing a lightweight low friction swing (flap) valve used as the sensing element 32 suspended vertically in the internal cavity 5 beneath the top housing 16. This sensing element 32 can pivot toward the proximal end 8 or the distal end 6 of the device 2 depending on the direction of the gas pulse flow. It will remain vertical with no flow and remain angled toward the direction of the gas pulse flow as long as the flow continues. It functions essentially the same as does the first embodiment with a distal transducer 40 and proximal transducer 22, except that the sensing element is not a pivotable fiber, but rather is a swing (flap) valve.

FIG. 11 illustrates a fourth embodiment wherein the sensing element 32 has a lightweight low friction swing (flap) valve suspended vertically in the internal cavity toward the distal end of the device 2. This design uses distal and proximal transducers which are IR light beam senders 48 and 46 and distal and proximal IR light beam receivers 52 and 50. When the gas pulse pushes the swing valve toward the distal end or proximal end of the device 2 the swing valve blocks the IR light path between the IR senders and receivers which transmit the direction and duration of the gas pulse flow to the microprocessor as in the prior three embodiments.

Figure 12:
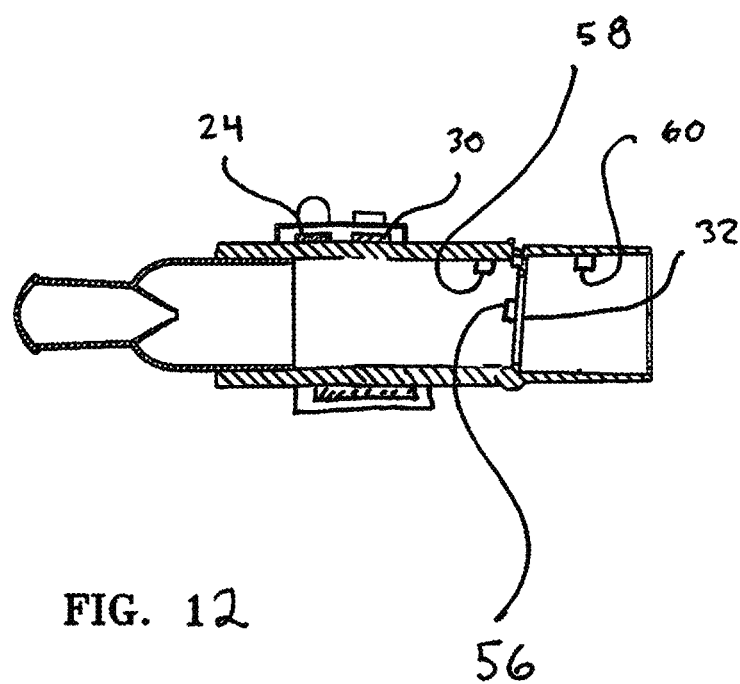
FIG. 12 is a right side cross sectional view of the fifth embodiment bidirectional incentive spirometer.

Looking at FIG. 12 a fifth embodiment device may be seen wherein rather than using IR light beam senders 48 and 46 and IR light beam receivers 52 and 50 as the transducer to signal swing valve movement direction and duration of the swing valve, there is a small magnet 56 placed on the valve and a pair of distal end and proximal end Hall Effect transducers 58 and 60 are used to detect gas pulse flow direction and duration as discussed herein. As can be seen in the first and third to fifth embodiments, the motion sensors 32 are basic in operation, using a swinging mechanical device with a simple mechanical swing motion transducer (Hall Effect sensor, opening/closing electrical contact switches or IR light beams) located somewhere in the internal cavity of the body 4. Upon contact of a gas pulse flow with the swinging mechanical device, its lightweight body swings out the way to initiate a signal through its transducer and to allow the gas pulse to pass through the device 2. In the second embodiment there are no moving parts but rather a flexing strain gauge and its transducer. As any motion sensor sees a passing gas pulse flow, the motion sensor provides an electrical signal to the microprocessor 30 which is converted into stored data to reflect time of occurrence, direction of gas pulse flow and duration of gas pulse flow.

Looking at FIGS. 13 and 14 a sixth embodiment device can be seen. This sixth embodiment is a stripped down version of first embodiment that utilizes the pivotable fiber as the sensing element 32 (with its distal and proximal transducers 40 and 42), the microprocessor 30 (with or without an integrated wireless transmitter), battery 20 and bottom housing 22, however, here the cycle initiation switch is a magnetic switch 70 that utilizes a removable magnet 72 to activate. There is an optional body motion detection device 74, preferably an accelerometer switch 74 mounted on the body 4 that operationally or functionally resides directly behind the magnetic switch 70 and the helps preserve the battery power by not allowing the device to be fully powered until the device is actually being handled or is in motion. In this way inadvertent activation of the magnetic switch 70 or failure to turn the magnetic switch 70 off will not run the battery down. The accelerometer switch 74 senses motion of the body 4 when it is handled, and it allows the passage of current for a preset period of time, generally not in excess of 5 minutes.

The motion sensor may be of various designs using Hall Effect sensors, mechanical sensors, strain gauges, IR light beams or any equivalent member who's sensing element alone or in conjunction with a transducer can generate an electric signal transmittable to the microprocessor 30.

In operation, the patient frictionally engages the appropriate respiratory device to the distal end port 6 of the bidirectional incentive spirometer. (Generally, this will first be a PEP device to first loosen the phlegm from the patient's lungs.) Then, they activate the cycle initiation switch 28 by removing the magnet, which turns on the device 2 provided that the accelerometer switch has also been activated by motion of the device 2 during handling. (Once the device 2 is put down and not moved for a preset period of time, the accelerometer switch turns the power off.) Once powered, the Microprocessor tests the illumination of the optional LED 18, and begins the recording of any gas pulse flow the sensing element 32 detects and sends to the microprocessor 30 or to the transducer 12 and then the microprocessor 30. For this PEP phlegm clearing cycle, the microprocessor 30 records the time the sensing element 32 reacts by motion or deflection to the gas pulses flowing by it, records the direction of flow and optionally, records the duration of the gas pulses encountered in the cycle. At every detection of a moving gas pulse past the sensing element 32 the microprocessor 30 will power the LED 18 to illuminate. The duration of this optional LED illumination may be for a preset period or may last as long as the sensing element 32 sees gas pulse movement. This will be preset in the microprocessor. The former indicates a gas pulse has occurred while the latter shows how long the gas pulse has persisted. The patient then removes the PEP device and connects the medicament delivery device and begins the drug delivery cycle. The gas pulses are again detected and recorded as in the PEP phlegm clearing cycle. Since the direction of the gas pulses are in the reverse direction as indicated by the sensing element 32, the microprocessor 30 can differentiate whether it is an exercise or a medicament delivery. When finished, the patient disconnects the medicament delivery device. At this time, all of the individual pulmonary events have been recorded and with the microprocessor 30 not receiving any gas pulse signals for a preset period of time, turns off. The technician may insert a memory stick signaling the microprocessor 30 to export all of its data onto the memory stick. Alternately, the technician may use their smart device (cell phone, tablet, computer etc.) to pair to the microprocessor 30 and initiate a data transfer from the microprocessor 30 via an application installed on the smart device.

The data provided by the microprocessor 30 will be in packets with each packet representing a pulmonary cycle the patient used the device 2 between the depressing of the cycle initiation switch 28 and the timing out of the device 2 by the microprocessor 30. It will chart the number of events, the date and time they occurred, the direction of the gas pulse flow, and optionally the duration of each gas pulse flow. With this data the medical staff can see the following:

If the patient performed all of their treatments.
If the PEP exercises were done with the correct number of repetitions.
If the PEP exercises were done at the prescribed times and frequency.
If the medicament dosage was administered as prescribed (correct in time, frequency and duration.)
If additional PEP exercises were performed or additional medicament was used, and when.

As described herein, the linear bidirectional incentive spirometer 2 allows connection to any PEP device, medicament delivery device or other pulmonary therapy device. Its linear design minimizes the amount of aerosol condensing on the devices inner walls, maximizes the aerosol particle size transmission efficiency, and monitors, records and sends a visual prompt when the lung clearing exercises are correctly performed. With this information the medical staff can correlate the patient's progress to their performance of phlegm clearing exercises and dosage of aerosol medicament. Therein, more informed medical decisions can be rendered.

The visual feedback of the device 2 provided by the LED 18 serves to instantaneously communicate to the end user (patient) that they are indeed operating the device 2 properly with pulses of exhaled air or pulses of inhaled medicament passing through the device 2. The data collected per phlegm clearing cycle or medicament cycle by the microprocessor, allows the medical practitioner to review the patient's progress against their adherence to the pulmonary treatment regime, to calculate the delivered drug dose for adjustment of the patient's medication and to place the patient's pulmonary treatment data into their medical record. This offers a huge step forward in the evaluation and review of the treatment of respiratory ailments.

It is to be understood that while not illustrated, any hard wire connections between components may be through wire raceways in the device body 2 (not illustrated) or may be routed on the outside or inside faces of the body as is well known in the art.

While certain features and aspects have been described with respect to exemplary embodiments, one skilled in the art will recognize that numerous modifications are possible. Consequently, although several exemplary embodiments are described above, it will be appreciated that the invention is intended to cover all modifications and equivalents within the scope of the following claims.

Having thus described the invention, what is claimed as new and desired to be secured by Letters Patent is as follows:

1. A bidirectional incentive spirometer for connection to and use with pulmonary treatment and drug delivery devices, comprising:
 a linear, hollow cylindrical body, having an exterior surface, a distal end port and a proximal end port, said body defining a linear cavity therebetween said distal end port and said proximal end port for a flow of a gas pulse;
 a singular motion sensor having a sensing element operationally positioned between said distal end port and said proximal end port within said body so as to detect said flow of said gas pulse, and a direction of gas pulse along an interior passage of said body;
 a battery affixed to said body;
 a microprocessor with a real time clock and a memory, said microprocessor affixed to said body;
 a cycle initiation switch comprising an external magnet removeably coupled to a magnetic switch extending from said body that when removed, provides power to said microprocessor of said spirometer;
 wherein said battery, said microprocessor and said cycle initiation switch are in operative communication with said motion sensor to collect data, said data including a date and time of the occurrence of a flow of said gas pulse and a direction of said flow of said gas pulse within said linear cavity when said motion sensor experiences a motion due to said flow of said gas pulse within said linear cavity; and
 a motion detection device affixed to said body that allows said cycle initiation switch to provide power to said microprocesser when said motion detection device senses motion of said spirometer.

2. The bidirectional incentive spirometer of claim 1 further comprising:
 a wireless transceiver for the transmission of said data, said wireless transceiver affixed to said body and connected to said microprocessor.

3. The bidirectional incentive spirometer of claim 2 wherein said motion sensor is selected from the group of motion sensors including Hall effect sensors, heated anemometers, bidirectional resistive strain sensors, flexible diaphragm pressure switches, swing make or break beam sensors and the functional equivalents, alone or in combination thereof.

4. The bidirectional incentive spirometer of claim 3 further comprising:
 a data collection port connected to said microprocessor;
 a battery housing affixed to said exterior surface said body, said battery residing therein said battery housing;
 an LED light;
 an external housing affixed to said body, wherein said microprocessor, said wireless transceiver, said LED light, said cycle initiation switch and said data collection port are housed therein said external housing.

5. The bidirectional incentive spirometer of claim 1 further comprising:
 a data collection port connected to said microprocessor.

6. The bidirectional incentive spirometer of claim 5 wherein said motion sensor is selected from the group of motion sensors including Hall effect sensors, heated anemometers, bidirectional resistive strain sensors, flexible diaphragm pressure switches, swing make or break contact switches, pivotable fibers or strands, bidirectional accelerometers, IR radio frequency beam sensors and the functional equivalents, alone or in combination thereof.

7. The bidirectional incentive spirometer of claim 1 wherein said motion sensor is selected from the group of motion sensors including Hall effect sensors, heated anemometers, bidirectional resistive strain sensors, flexible diaphragm pressure switches, swing make or break contact switches, pivotable fibers or strands, bidirectional accelerometers, IR radio frequency beam sensors and the functional equivalents, alone or in combination thereof.

8. The bidirectional incentive spirometer of claim 1 wherein said proximal end port is a 15 mm ID female port and the distal end port is a 22 mm OD male port.

9. The bidirectional incentive spirometer of claim 1 wherein said data also comprising a duration of said occurrence of said flow of said gas pulse based on a length of time when said motion detector experiences a motion due to said flow of said gas pulse within said linear cavity.

10. A bidirectional incentive spirometer for connection to and use with pulmonary treatment and drug delivery devices, comprising:
 a linear, hollow cylindrical body, having an exterior surface, a distal end port and a proximal end port, said body defining a linear cavity therebetween said distal end port and said proximal end port for a flow of a gas pulse;
 at least one motion sensor having a sensing element operationally positioned between said distal end port and said proximal end port within said body so as to detect said flow of said gas pulse, and a direction of gas pulse along an interior passage of said body;
 a battery affixed to said body;
 a microprocessor with a real time clock and a memory, said microprocessor affixed to said body;
 a magnetic cycle initiation switch operationally connected between said battery and said microprocessor, comprising a magnet removeably coupled to a magnetic switch that when removed allows said magnetic switch to provide power to said microprocessor;
 a motion activated accelerometer switch operationally connected between said battery and said microprocessor;
 wherein said battery, said microprocessor, said cycle initiation switch and said accelerometer switch are in operative communication with said motion sensor so as to collect data, said data including a date and time of the occurrence of a flow of said gas pulse and a direction of said flow of said gas pulse within said linear cavity when said motion detector experiences a motion due to said flow of said gas pulse within said linear cavity.

11. The bidirectional incentive spirometer of claim 10 further comprising:
a wireless transceiver for the transmission of said data, said wireless transceiver affixed to said body and connected to said microprocessor.

12. The bidirectional incentive spirometer of claim 11 wherein said motion sensor is selected from the group of motion sensors including Hall effect sensors, heated anemometers, beam sensors and the functional equivalents, alone or in combination thereof.

13. The bidirectional incentive spirometer of claim 12 further comprising:
a data collection port connected to said microprocessor;
a battery housing affixed to said exterior surface said body, said battery residing therein said battery housing; and
an external housing affixed to said body, wherein said microprocessor, said wireless transceiver, said cycle initiation switch and said data collection port are housed therein said external housing.

14. The bidirectional incentive spirometer of claim 10 further comprising:
a data collection port connected to said microprocessor.

15. The bidirectional incentive spirometer of claim 14 wherein said motion sensor is selected from the group of motion sensors including Hall effect sensors, heated anemometers, bidirectional resistive strain sensors, flexible diaphragm pressure switches, swing make or break contact switches, pivotable fibers or strands, bidirectional accelerometers, IR radio frequency beam sensors and the functional equivalents, alone or in combination thereof.

16. The bidirectional incentive spirometer of claim 10 wherein said motion sensor is selected from the group of motion sensors including Hall effect sensors, heated anemometers, bidirectional resistive strain sensors, flexible diaphragm pressure switches, swing make or break contact switches, pivotable fibers or strands, bidirectional accelerometers, IR radio frequency beam sensors and the functional equivalents, alone or in combination thereof.

17. The bidirectional incentive spirometer of claim 10 further comprising a motion detection device affixed to said body that allows said cycle initiation switch to provide power to said microprocesser when said motion detection device senses motion of said spirometer.

18. The bidirectional incentive spirometer of claim 10 wherein said proximal end port is a 15 mm ID female port and the distal end port is a 22 mm OD male port.

19. The bidirectional incentive spirometer of claim 10 further comprising an LED light connected to said microprocessor to visually indicate when said motion sensor senses motion; and
wherein said data also comprises duration of said occurrence of said flow of said gas pulse based on a length of time when said motion detector experiences a motion due to said flow of said gas pulse within said linear cavity.

* * * * *